United States Patent [19]

Jacobs et al.

[11] Patent Number: 5,571,682
[45] Date of Patent: Nov. 5, 1996

[54] CALIBRATING AND TESTING IMMUNOASSAYS TO MINIMIZE INTERFERENCES

[75] Inventors: Merrit N. Jacobs, Fairport; Paul A. Kildal-Brandt, Webster; Thomas C. Arter, Rochester, all of N.Y.

[73] Assignee: Johnson & Johnson Clinical Diagnostics, Inc., Rochester, N.Y.

[21] Appl. No.: 363,099

[22] Filed: Dec. 22, 1994

[51] Int. Cl.$^6$ ................................................. G01N 33/53
[52] U.S. Cl. ................... 435/7.9; 435/7.92; 435/7.93; 435/7.94; 435/7.95; 435/28; 435/962; 435/970; 436/517; 436/518; 436/536; 436/805; 436/815
[58] Field of Search .................... 422/119, 56–58; 436/517, 518, 805, 536; 435/7.9, 7.92–7.95, 28, 962, 970; 356/433, 445, 448

[56] References Cited

U.S. PATENT DOCUMENTS

| | | | |
|---|---|---|---|
| 4,022,577 | 5/1977 | Brooker et al. | 436/517 |
| 4,184,923 | 1/1990 | Schubert | 435/28 |
| 4,835,110 | 5/1989 | Seymour et al. | 436/517 |
| 5,171,688 | 12/1992 | Hewett et al. | 435/28 |

FOREIGN PATENT DOCUMENTS 2167446  8/1989  Japan .

Primary Examiner—Carol A. Spiegel
Attorney, Agent, or Firm—Dana M. Schmidt

[57] ABSTRACT

A method for reducing interferent bias such as hemoglobin bias in immunoassays using dried slide test elements featuring peroxidase and leuco dye as the labeling mechanism. The method features the steps of:

a) calibrating an immunoassay of a target analyte by ascertaining the time at which the rate of change in density produced by a first set of the test elements for the target analyte on at least one liquid having a known amount of interferent of choice and a known amount of target analyte, crosses over or minimizes the difference compared to the rate of change in density produced by a second set of test elements substantially identical to the first set of test elements, on a liquid having the known amount of target analyte but a negligible amount of interferent of choice, and b) conducting an assay of a patient sample of unknown amount of the target analyte by reading the rate of change in density in a third set of the test elements substantially identical to the first and second sets, caused by the sample, at a time corresponding to the cross-over time ascertained in step a).

3 Claims, 7 Drawing Sheets

(COMPETITIVE ASSAY)

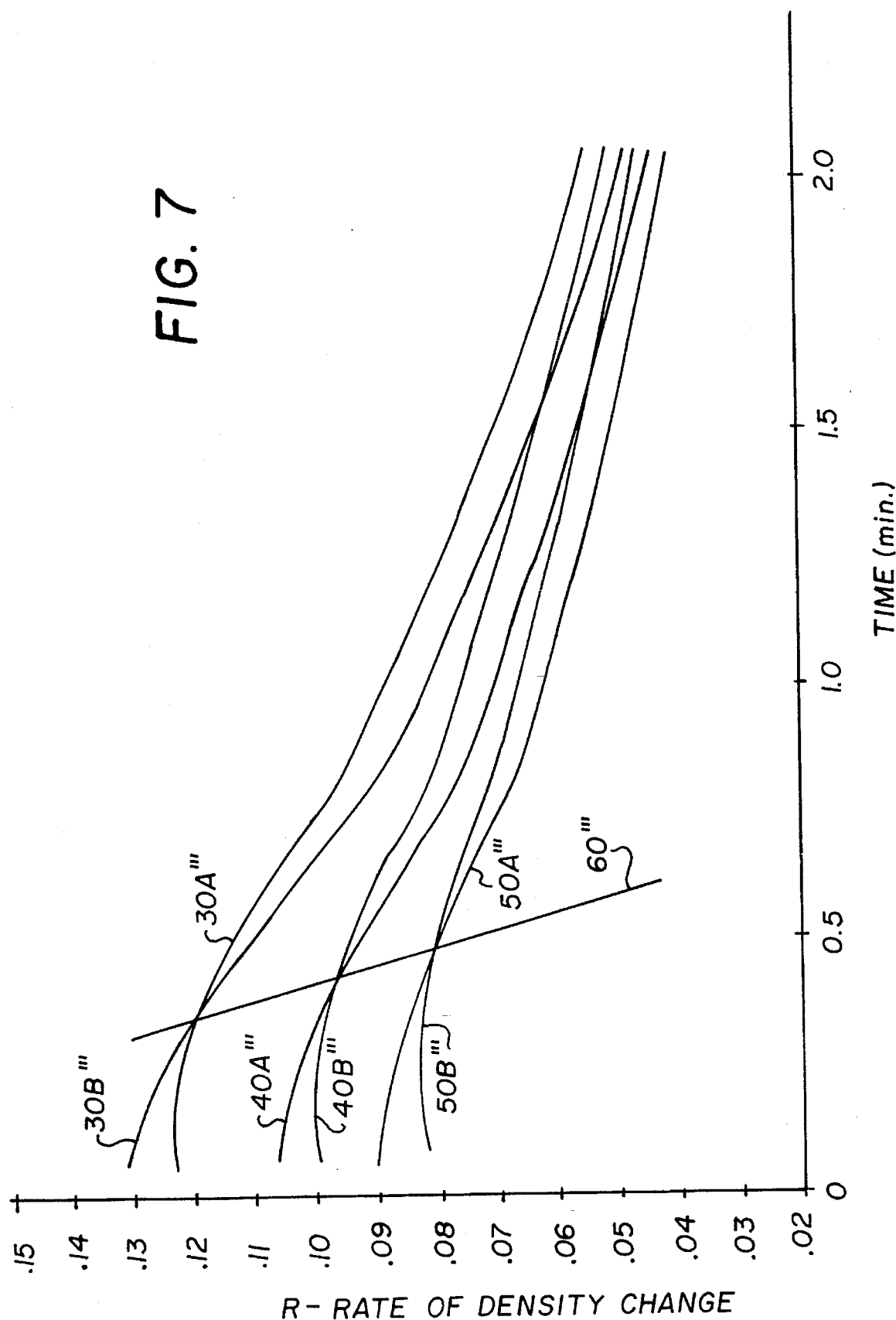

CALIBRATING AND TESTING IMMUNOASSAYS TO MINIMIZE INTERFERENCES

FIELD OF INVENTION

This invention relates to a method of calibrating and testing immunoassays that are susceptible to interferences, especially hemoglobin, using dried slide test elements.

BACKGROUND OF THE INVENTION

Immunoassays are commonly done as rate assays, that is, they are measured as a rate of change over time, for example, the rate of increase or decrease in density of a dye. The dye chemistry can be, for example, one that relies upon an enzyme to catalyze a leuco dye to change into a colored dye. A class of enzymes that is frequently used for this purpose is oxidases, preferably peroxidase, or "POD". Most preferably, the peroxidase is horseradish peroxidase, hereinafter "HRP".

Immunoassays involve the measurement of limited amounts of POD, unlike other assays which can use excess amounts of POD. (Excess amounts of course are relatively insensitive to interferents that imitate or react with the POD.) An immunoassay is usually either "competitive" or "sandwich". In "competitive" assays, a labeled analog of the target analyte to be determined is placed in competition with the analyte for a fixed amount of an appropriate, immobilized antibody which can react with either the target analyte or a target analyte analog. The label on the analog can be appropriately detected in either its "free" or its complexed (that is, reacted) form. Signal level then will tell the user how much target analyte is in the sample being tested.

In the alternative immunoassay format of a "sandwich" immunoassay or immunometric assay, the target analyte is contacted with two or more receptor molecules, e.g., antibodies, which bind to the target analyte at different epitopic sites. One receptor molecule is typically appropriately labeled and the other is either immobilized on a solid substrate, or is capable of being immobilized thereon. The amount of target analyte is directly proportional to the amount of bound complex among the target analyte and the two receptors.

In either of these assays, if HRP is used, it is part of the "label". Hence, immunoassays cannot rely on the presence of excessive amounts of HRP to overcome changes due to the presence of interferents.

It has been known in the art that such peroxidase chemistry, when used in immunoassays, is interfered with by substances such as hemoglobin. That is, the presence of any hemoglobin will cause more or less of a bias. In liquid immunoassays, this is corrected by diluting, usually. Such correction by dilution is not available, however, when using slide test elements. The reason is that it complicates the procedure, adds errors, and further lowers an already low concentration of certain analytes. Since hemoglobin is often present in blood samples in unknown amounts, it has been a long-felt problem prior to this invention to somehow correct for the unpredictable bias created by hemoglobin in such immunoassays. Certainly a correction could be done if the amount of hemoglobin present (if any) were first ascertained, but that is a step most laboratories do not wish to do prior to running the immunoassay.

SUMMARY OF THE INVENTION

We have discovered some properties of the hemoglobin interference that have allowed us to overcome the above-noted problems. That is, we have discovered a) that the rate of impact of interferents such as hemoglobin at a fixed concentration, i.e., the bias effect, varies depending on the concentration of the analyte; and b) that the rate of change of the signal produced by a selected amount of target analyte and a fixed amount of interferent, e.g., hemoglobin, say 250 mg/dl, decreases over time faster than the rate of change of signal produced by that same amount of target analyte with zero amount of interferent (hemoglobin). This last means that we have discovered there is a cross-over point in time, defined hereinafter, for any level of any immunoassay analyte, at which the hemoglobin bias becomes zero or a steady-state minimum. It is particularly the latter cross-over time that has led to the invention.

More specifically, in accord with one aspect of the invention, there is provided a method of reducing bias caused by an interferent of choice when conducting immunoassays using a dried test element containing detection reagents comprising peroxidase and a substrate that produce a detectable density change at various rates, wherein the peroxidase is present in a predetermined, limited amount. The method comprises the steps of:

a) calibrating an immunoassay of a target analyte by ascertaining the time at which the rate of change in density produced by a first set of said test elements for said target analyte contacted with at least one liquid having a known amount of interferent of choice and a known amount of target analyte, crosses over or minimizes at a cross-over time, the rate of change in density produced by a second set of test elements substantially identical to said first set of test elements, contacted with a liquid having said known amount of target analyte but a negligible amount of interferent of choice, and b) conducting an assay of a patient sample of unknown amount of said target analyte by reading the rate of change in a selected element of said test elements of said first or second sets, caused by said sample contacting said selected element, at a time corresponding to said cross-over time ascertained in step a).

In accord with another aspect, there is provided a calibration method of reducing hemoglobin bias in calibration values for testing for a target analyte in an immunoassay that uses horseradish peroxidase and a substrate to produce a dye density that changes over time. The method comprises the steps of:

a) ascertaining for a plurality of times using some of a plurality of slide test elements of identical composition, the rate of change in the dye density produced at least by two liquids having two different preselected known amounts of the target analyte and no amounts of hemoglobin;

b) ascertaining for the same plurality of times using additional members of the slide test elements of identical composition, the rate of change in the dye density produced by at least two liquids which have added to them, a preselected non-negligible amount of hemoglobin that is the same for both of the at least two liquids;

c) determining the points in time when the rate of change of the at least two liquids containing the non-negligible amounts of hemoglobin, cross-over or minimize the rate of change for the corresponding two liquids lacking however any hemoglobin, thereby producing cross-over times having a minimized bias; and d) selecting said cross-over time for one of the at least two liquids as the optimal read time for subsequent sample testing having an initial rate of change corresponding to said one of said at least two liquids.

In accord with still another aspect of the invention, there is provided a method for testing patient body fluids for a target analyte to reduce any hemoglobin bias, in an immunoassay that uses horse radish peroxidase and a leuco dye to produce a dye density that changes over time, the method comprising the steps of a) ascertaining the rate of change in density over time of a particular patient body fluid of an unknown amount of the analyte, in an analyzer having at least one assigned cross-over point in time as an optimal read time calculated in accordance with the calibration method noted above;

b) selecting a fixed point in time prior to any of the assigned cross-over times as an initial read time;

c) ascertaining from the point in time selected in step b), the initial rate for that time from the values ascertained in step a);

d) ascertaining for the initial rate ascertained from step c) an optimal cross-over read time that corresponds to the initial rate; and e) ascertaining from the rates determined in step a) the rate of change of the patient sample corresponding to the optimal read time.

(As used herein, "single generation" means, the test elements for a particular analyte, verified to have equivalent performance at any given concentration of analyte, whether or not manufactured in a single event.)

Accordingly, it is an advantageous feature of the invention that rate immunoassays can be conducted using a POD detection scheme, while at the same time reducing the bias that is normally created when certain interferents are present.

Other advantageous features will become apparent from the Detailed Description which follows, when read in light of the attached drawings.

BRIEF DESCRIPTION OF THE DRAWINGS

FIGS. 6 and 7 are plots similar to that of FIG. 3, but illustrating actual working examples for phenytoin and digoxin, respectively.

DESCRIPTION OF THE PREFERRED EMBODIMENTS

Figure 1:
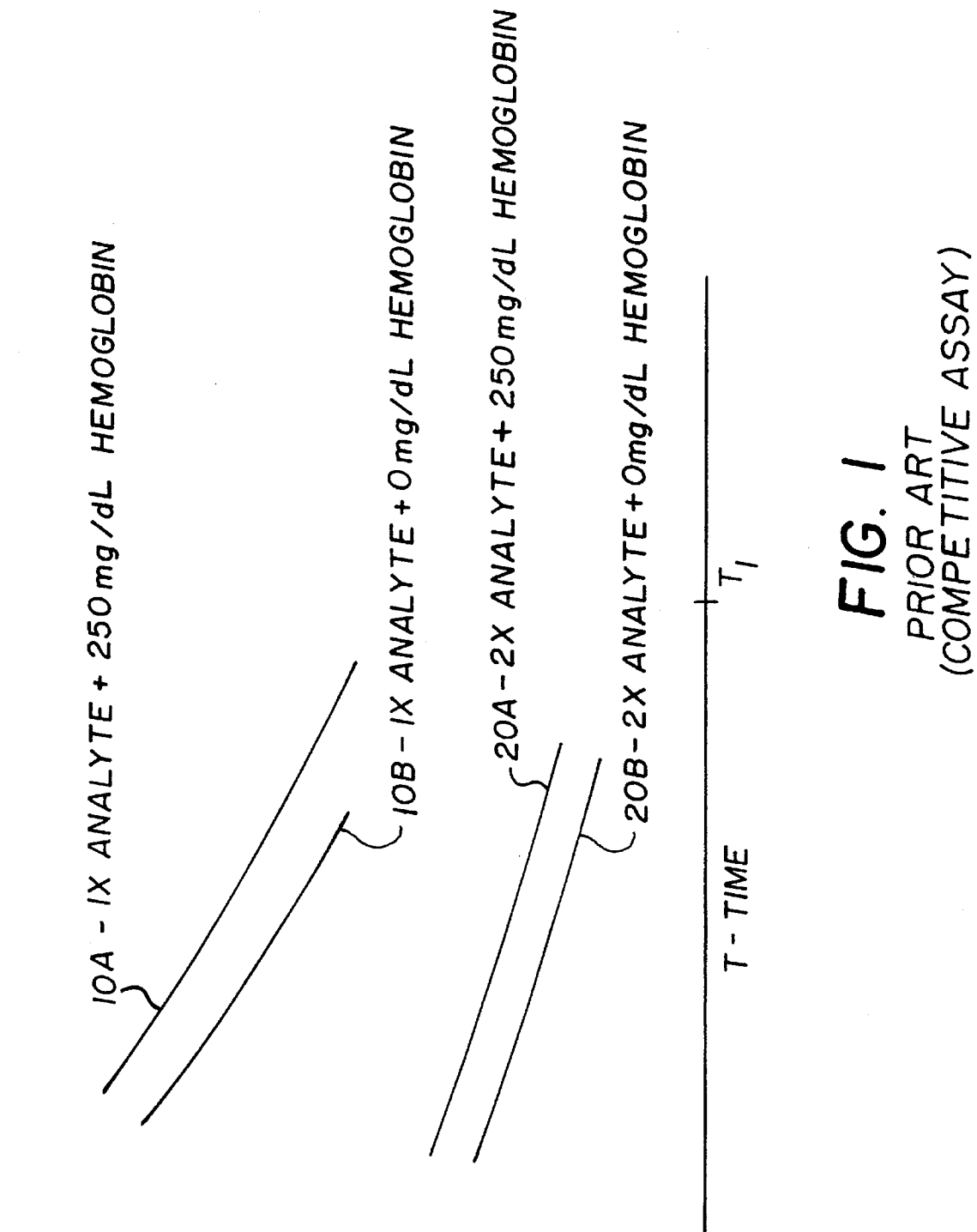
FIG. 1 is a plot of rate of density change versus time as was known in the prior art for 1× and 2× amounts of a particular immuno-analyte, with say 250 mg/dl hemoglobin and with no hemoglobin, respectively.

The discussion hereinafter is addressed to certain preferred embodiments, wherein a cross-over time is ascertained for a first liquid having x amount of the target analyte and a non-negligible amount of hemoglobin, and a second liquid having said x amount of the target analyte and zero amount of hemoglobin. In addition, the invention is useful for interferents other than hemoglobin, or if the second liquid has a negligible amount of hemoglobin, which as used herein means from zero to about 50 mg/dl, and where the two liquids never reach a time in which their rates are exactly equal. Hence, as used herein, "cross-over" means, when the rates of change of the slide test elements bearing the respective two liquids are either substantially the same, or, when they first reach a steady-state minimum difference having minimized bias a condition that can occur especially for very low levels of target analyte.

Additionally, the preferred embodiments feature assays in which the rate of change of dye density for a given immunoassay decreases over time as shown for particular preferred analytes, and wherein the optimal read time values are shown as a continuous polynomial curve determined by using more than two, i.e., three cross-over points from three calibrator liquids of a known hemoglobin concentration. In addition, the invention is useful for sandwich and competitive immunoassays regardless of the analyte of choice, and regardless of whether the optimal read times are a graphic plot or look-up table, calculated as a polynomial function or a linear function from more than two cross-over points of calibrators, or only two, respectively; so long as the immunoassay chemistry uses POD to produce the dye density.

Thus, the invention is described for the particular preferred immuno-analytes, that is, phenytoin and digoxin, corrected for hemoglobin bias. Other interferent biases can be reduced in a similar manner, if the interferent, hereinafter "interferent of choice", produces a cross-over point in time as herein defined, of the measured rates of change, when tested with both negligible and non-negligible amounts of the interferent, respectively. Other examples of such interferents include: reducing agents such as gentisic acid, ascorbic acid, dipyrone, etc.

The preferred slide test elements for assaying phenytoin and digoxin comprise the following:

Slide Test Elements for Detection of Digoxin

Elements for the detection of digoxin were prepared using conventional procedures and the general structure of slide test elements available under the trademark "Ektachem"® from the Clinical Diagnostics Division, formerly of Eastman Kodak Co., but having the following coating formulations. The gravure and receptor coatings detailed below diffused into the porous spreading coating to form separate zones near the boundaries of the dried porous spreading layer.

| Element Structure | | |
|---|---|---|
| | | Dry Coverage (g/m²) |
| [gravure coating] | Digoxin-horseradish peroxidase | $6 \times 10^{-6}$ |
| | Bovine serum albumin | $2.15 \times 10^{-4}$ |
| | 3',5'-Dichloro-4'-hydroxyacetanilide | $9.95 \times 10^{-3}$ |
| | 3-(N-morpholino)-propanesulfonic acid buffer (pH 7) | $4.50 \times 10^{-3}$ |
| | TRITON ™ X-100 nonionic surfactant | $4.30 \times 10^{-3}$ |
| | Polyacrylamide | $1.08 \times 10^{-3}$ |

| Element Structure | | Dry Coverage (g/m²) |
|---|---|---|
| [Spreading layer] | 4,5-Dihydroxy-3-(6,8-disulfo-2-naphthylazo)-2,7-napthalenedisulfonic acid, sodium salt | 5.38 × 10⁻² |
| | Poly(vinyltoluene-co-methacrylic acid) (98:2 weight ratio) beads (30 μm average diameter) | 130 |
| | Poly(methyl acrylate-co-sodium 2-acrylamido-2-methylpropansulfonate-co-2-acetoacetoxyethyl methacrylate) (90:4:6 weight ratio) | 2.583 |
| | N-[tris(hydroxymethyl)methyl]-2-aminoethanesulfonic acid buffer (pH 7) | 0.219 |
| | Dimedone | 0.45 |
| | 4,5-bis(4-dimethylaminophenyl)-2-(3,5-dimethoxy-4-hydroxyphenyl)-imidazole leuco dye | 0.2 |
| | 3',5'-Dichloro-4'hydroxyacetanilide | 0.22 |
| | Bovine serum albumin | 1.0 |
| | Mannitol | 1.0 |
| | Vanadyl sulfate | 0.04 |
| | Glycerol | 2.0 |
| | Anti-digoxin monoclonal antibodies covalently attached to poly[styrene-co-p-(2-chloroethylsulfonylmethyl)styrene] (95:5 weight ratio) beads (0.5 μm average diameter) | 0.015 |
| [Reagent Layer Coating] | Hardened gelatin | 10.15 |
| | N-[tris(hydroxymethyl)-methyl]-2-aminoethane-sulfonic acid buffer (pH 7) | 4.58 |
| | TRITON ™ X-100 nonionic surfactant | 0.02 |
| | 3',5'-dichloro-4'-hydroxyacetanilide | 0.44 |
| | Poly(ethylene terephthalate) support | |

Slide Test Elements for Detection of Diphenylhydantoin (Phenytoin)

Such elements were prepared similarly to those described above for digoxin except that they had reagents suitable for detection of diphenylhydantoin. The elements were coated using conventional procedures and equipment and had the following basic coating compositions and structure:

| Element Structure | | Dry Coverage (g/m²) |
|---|---|---|
| [gravure coating] | Diphenylhydantoin-horseradish peroxidase conjugate | 1.3 × 10⁻⁵ |
| | Bovine serum albumin | 2.15 × 10⁻⁴ |
| | 3',5'-dichloro-4'-hydroxyacetanilide | 9.95 × 10⁻³ |
| | 3-(N-morpholino) propanesulfonic acid buffer (pH 7) | 4.50 × 10⁻³ |
| | TRITON ™ X-100 nonionic surfactant | 4.30 × 10⁻³ |
| | Polyacrylamide | 1.08 × 10⁻³ |
| | 4,5-dihydroxy-3-(6,8-disulfo-2-naphthylazo)-2,7-napthalene-disulfonic acid, sodium salt | 5.38 × 10⁻² |
| [Spreading Layer] | Poly(vinyltoluene-co-methacrylic acid) (98:2 weight ratio) beads (30 μm average diameter) | 130 |
| | Poly(methyl acrylate-co-sodium 2-acrylamido-2-methylpropanesulfonate-co-2-acetoacetoxyethyl methacrylate) (90:4:6 weight ratio) | 2.583 |
| | N-[tris(hydroxymethyl)methyl]-2-aminoethanesulfonic acid buffer (pH 7) | 0.219 |
| | Olin Surfactant 10G nonionic surfactant | 0.238 |
| | Dimedone | 0.45 |
| | 3',5'-dichloro-4'-hydroxyacetanilide | 0.22 |
| | Bovine serum albumin | 1.0 |
| | Mannitol | 1.0 |
| | Vanadyl sulfate | 0.04 |
| | Glycerol | 2.0 |
| [Receptor Layer] | Poly(N-isopropylacrylamide-co-2-hydroxyethyl methacrylate-co-N,N'-methylenebisacrylamide) (85:10:5 weight ratio) | 0.5 |
| | 4,5-bis(4-dimethylaminophenyl)-2-(3,5-dimethoxy-4-hydroxyphenyl)-imidazole leuco dye | 0.2 |
| | N-[tris(hydroxymethyl)methyl]-2-aminoethanesulfonic acid buffer (pH 7) | 0.1 |
| | TRITON ™ X-100 nonionic surfactant | 0.02 |
| | TETRONIC ™ T908 nonionic surfactant | 0.02 |
| | Olin surfactant 10G nonionic surfactant | 0.01 |
| | Dimedone | 0.05 |
| | Anti-diphenylhydantoin monoclonal antibodies covalently attached to poly[styrene-co-p-(2-chloroethylsulfonylmethyl)styrene](95:5 weight ratio) beads (1.0 μm average diameter) | 0.015 |
| [Reagent Layer] | Hardened gelatin | 10.15 |
| | N-[tris(hydroxymethyl)methyl]-2-aminoethanesulfonic acid buffer (pH 7) | 4.58 |
| | TRITON ™ X-100 nonionic surfactant | 0.02 |
| | 3',5'-dichloro-4'-hydroxyacetanilide | 0.44 |
| | Poly(ethylene terephthalate) support | |

The Prior Art

Referring now to FIG. 1, the prior art (mostly solution assays) was aware of the "positive" bias created by the presence of the hemoglobin interferent, as shown by curve 10A and curve 10B, or curve 20A compared to curve 20B. (Curve 20A differs from 10A only in that 20A is the plot of the rate for an analyte that is present in 2× the amount present for curve 10A.) However, the curves had been tracked only as far as Time $T=T_1$, during which time curves 10A and 10B are essentially co-parallel, and curves 20A and 20B are essentially co-parallel (in a competitive assay).

The Invention

We have discovered that, for certain peroxidase-driven target immunoassays using dried slide test elements, such as for digoxin and phenytoin, if the rate is allowed to run for a time $T>T_1$, the paired curves will be found to converge to a cross-over time $T_2$ or $T_3$, where $T_2$ and $T_3>T_1$. E.g., FIG. 2, curve 10A' substantially equals the rate of curve 10B' at time $T_2$, and curve 20A' substantially equals the rate of curve 20B' at time $T_3$. (In these cases, the "cross-over" is a point of substantial equality, but as noted herein, it can be a point in time of steady-state minimal difference.) As in the case of FIG. 1, curves 10A' and 20A' each have a definite amount of hemoglobin interferent present, e.g., 250 mg/dL, whereas 10B' and 20B' have none. The curves 20A' and 20B' represent 2× the amount of analyte of curves 10A' and 10B'.

Figure 2:
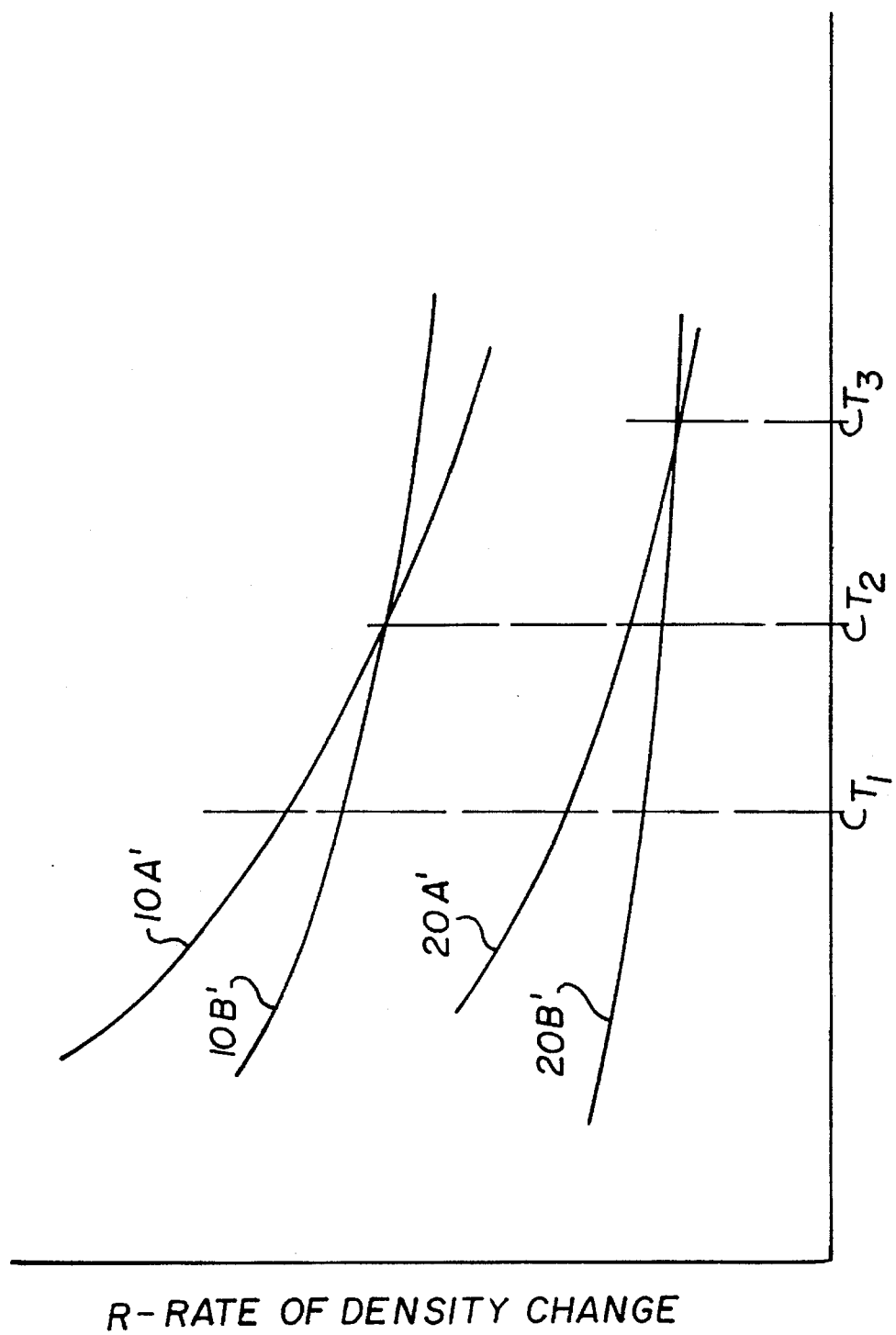
FIG. 2 is a similar plot except that it illustrates our discovery that indeed, the curves for zero amount of hemoglobin and a fixed amount, say 250 mg/dl hemoglobin, at any particular concentration of immuno-analyte, do have a cross-over time $T_i$ that is different at different concentration values of the immuno-analyte.

This cross-over phenomenon of FIG. 2 represents, of course, the point of minimum hemoglobin bias, and the optimal point in time when the unknown sample should be read for its rate, for this particular concentration of target analyte, e.g., 1× amount for curves 10A' and 10B'. Of course, one does not know in advance what the analyte concentration is, nor the amount of hemoglobin, so the rest of the method of the invention is a procedure whereby an "optimal" time of reading is selected that is close to, if not exactly the same as, the cross-over time for that exact amount of target analyte. Hence, the amount of bias from hemoglobin is minimized.

Figure 3:
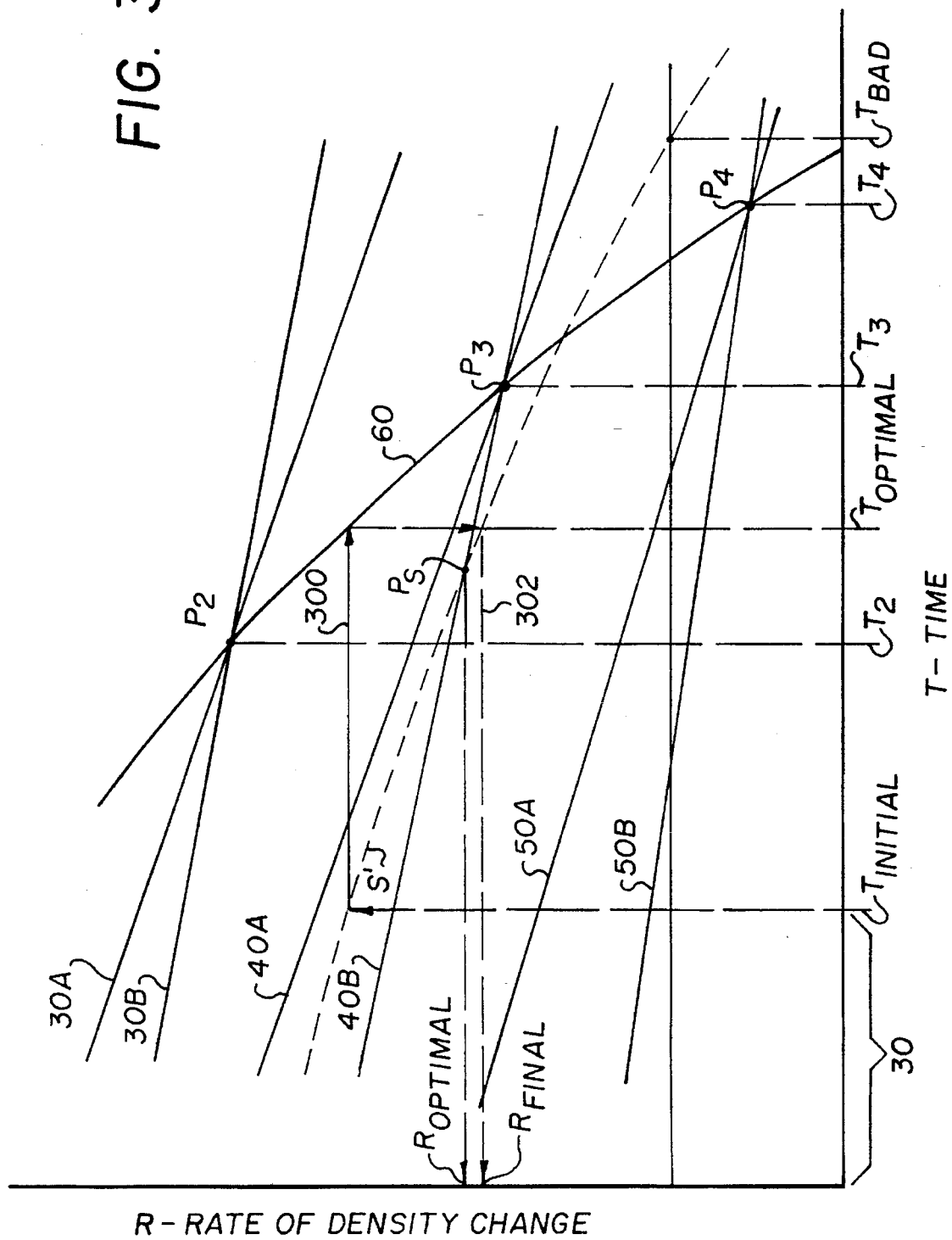
FIG. 3 is a plot similar to that of FIG. 2 except it illustrates the calibration method of the invention wherein calibrator fluids $C_1$, $C_2$, and $C_3$ are selected each with a known but different level of concentration of immuno-analyte.

Referring next to FIG. 3, the calibration portion of the invention is illustrated therein. That is, calibration is conventionally achieved by taking a set of slide test elements that are substantially identical, all for the same target immuno-analyte, for example digoxin, and testing on an analyzer one, two or three calibrator fluids of varying concentration ($C_1$, $C_2$, and $C_3$) of the target immuno-analyte, to determine their rate of change over time using some of said set of test elements. Such testing produces, FIG. 3, curves 30B, 40B, and 50B, respectively. These liquids however have negligible, e.g., zero, amounts of hemoglobin.

In accord with one aspect of the invention, the calibration procedure adds to this, the steps of ascertaining the similar rate curves 30A, 40A, and 50A, using other of said set of slide test elements on the same analyzer, using however calibration liquids having concentrations $C_1$, $C_2$, or $C_3$, respectively, and a non-negligible amount of hemoglobin, e.g., 250 mg/dl. (For convenience, the non-negligible amount of hemoglobin is the same for all of these additional calibration liquids, but it need not be. That is, one could have 250 mg/dl and another, only 200 mg/dl.) Because the plot 60 of "optimal" cross-over points, discussed hereinafter, is not in this case vertical, it is preferred that at least two pairs of rate curves be ascertained, that is both pairs 30A, 30B, and 40A, 40B; or both 30A, 30B and 50A, 50B; or both 40A, 40B and 50A, 50B. Most preferably, all three pairs of curves or data points are ascertained, in the event, as shown in FIG. 3, curve 60 is not linear. (A linear curve can be adequately defined by only two pairs of such curves.)

Having ascertained the data points for curves 30A, 30B; 40A, 40B; and 50A, 50B; the next step is to determine the points in time when each pair of curves reaches its cross-over time. In FIG. 3, those are, respectively, times $T_2$, $T_3$, and $T_4$, when the rates of change within a pair are substantially equal (shown as points $P_2$, $P_3$, and $P_4$). These times are each the optimal read time for that particular concentration of immuno-analyte in sample liquids, if such concentrations can be known or approximated. That is, the invention can be practiced by picking only one of these cross-over points for the corresponding concentration of analyte, regardless of whatever read times are used at other analyte concentrations.

Most preferably, instead of working with only two or three tested cross-over points, an extrapolation is made between and beyond those points, e.g., even at earlier times, to obtain curve 60, FIG. 3. That is, the next step is to calculate the corresponding cross-over points in time for analyte concentrations other than $C_1$, $C_2$, or $C_3$. This of course is done by interpolating the other cross-over points, by best-fitting a curve to points $P_2$, $P_3$, and $P_4$. Generically, such a curve is characterized by a polynomial of the formula time (of optimal read) $=A_0+A_1.\text{Rate}+A_2.(\text{Rate})^2$, where $A_0$, $A_1$, and $A_2$ are constants. If there are only two data points, such as $P_2$ and $P_3$, or $P_2$ and $P_4$, or $P_3$ and $P_4$, the curve degenerates into a linear curve of the formula $\text{Time}=A_0+A_1.\text{Rate}$. Whatever the curve shape for curve 60, it represents the assigned cross-over points in time from which a table of optimal read times can be constructed for subsequent testing of patient samples of unknown concentration and hemoglobin content.

Figure 4:
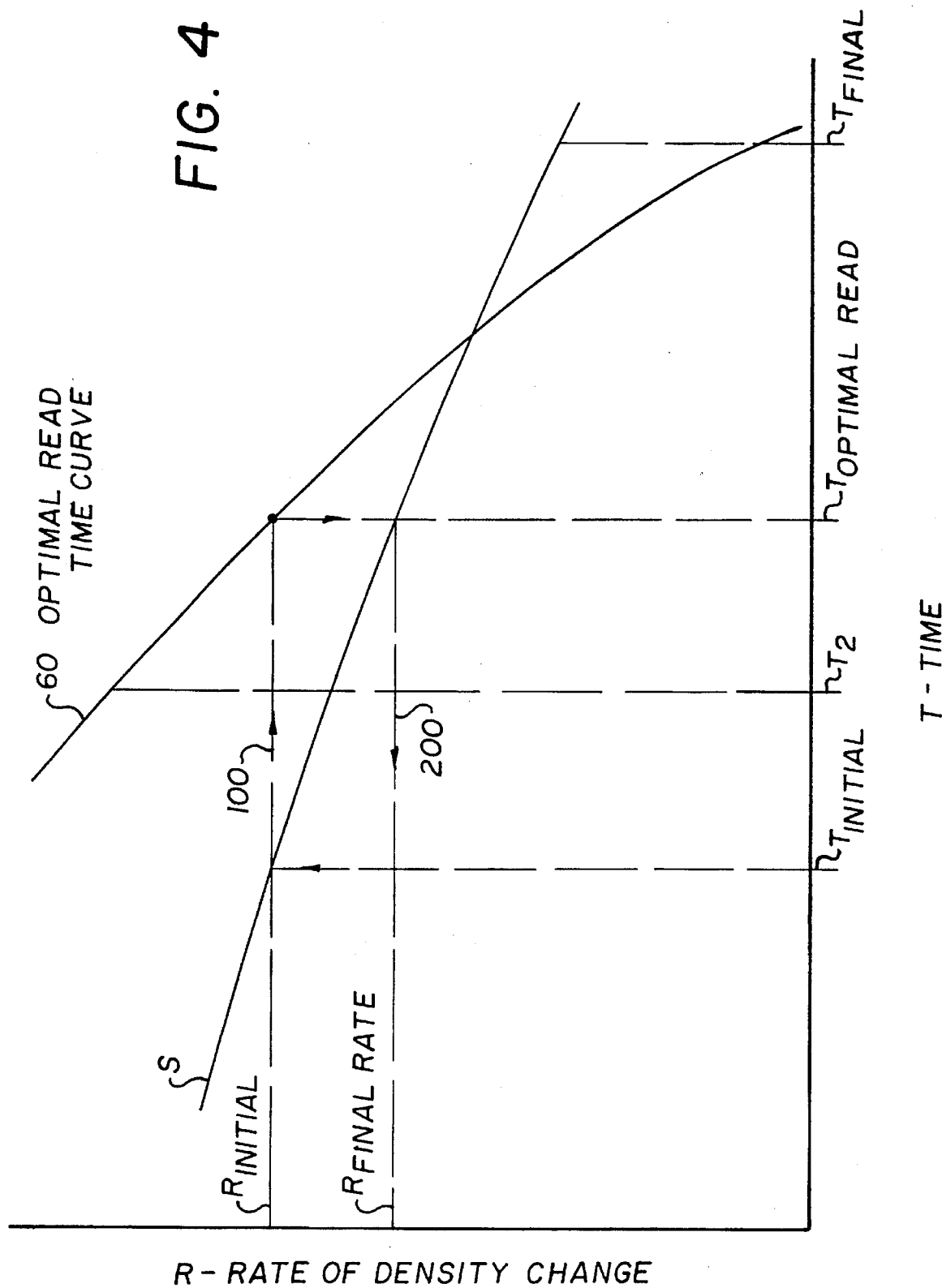
FIG. 4 is a plot similar to that of FIG. 3, but illustrating how the calibration plot obtained in FIG. 3 is used to test for an unknown concentration of a patient sample using the assigned optimal read time curve of FIG. 3.

In accord with another aspect of the invention, the test procedure on such a patient sample is as follows, using such curve 60, FIG. 4.

Using another one of said set of identical slide test elements, the patient sample is deposited and the rate of change detected in the same kind of analyzer used for the calibration. An extensive set of data points, represented by curve S (for "sample"), is ascertained, from at least time $T_{initial}$ to a time $T_{final}$. At a fixed time $T_{initial}$, which is early in the read times (e.g., averaged over the first 30 sec.), the corresponding rate of change $R_{initial}$ for that sample is ascertained. From that value of $R_{initial}$, the corresponding optimal read time $T_{optimal}$ read is selected from curve 60, arrow 100. That optimal read time is then used, on curve S, to ascertain (arrow 200) the "final" rate of change at that optimal time, that is then conventionally converted (from a calibration table) into a concentration.

Alternatively, $T_{initial}$ can be taken during the time periods covered by curve 60, provided that said same $T_{initial}$ is used throughout all assays.

That this indeed is a read time that minimizes the bias from hemoglobin can be seen from the hypothetical example plotted as dotted curve S' on FIG. 3. Assume that, in fact, its analyte concentration is $C_2$, a fair assumption given its location close to curve 40B. At time $T_{initial}$, an initial rate is ascertained which is arrow 300. This produces on curve 60, an optimal read time $T_{optimal}$, which then produces from curve S', a final rate $R_{final}$ as shown, arrow 302. It turns out, however, that this is NOT the final rate that has zero hemoglobin bias, since that zero bias final rate reading is $R_{optimal}$, just above $R_{final}$. $R_{optimal}$, of course, is the value corresponding to the actual cross-over point $P_S$, where curve S crosses over curve 40B. Nevertheless, this is a value for $R_{final}$ that is much closer to $R_{optimal}$ than most other readings that could be selected from curve S', e.g., at a time $T_{bad}$.

Figure 5:
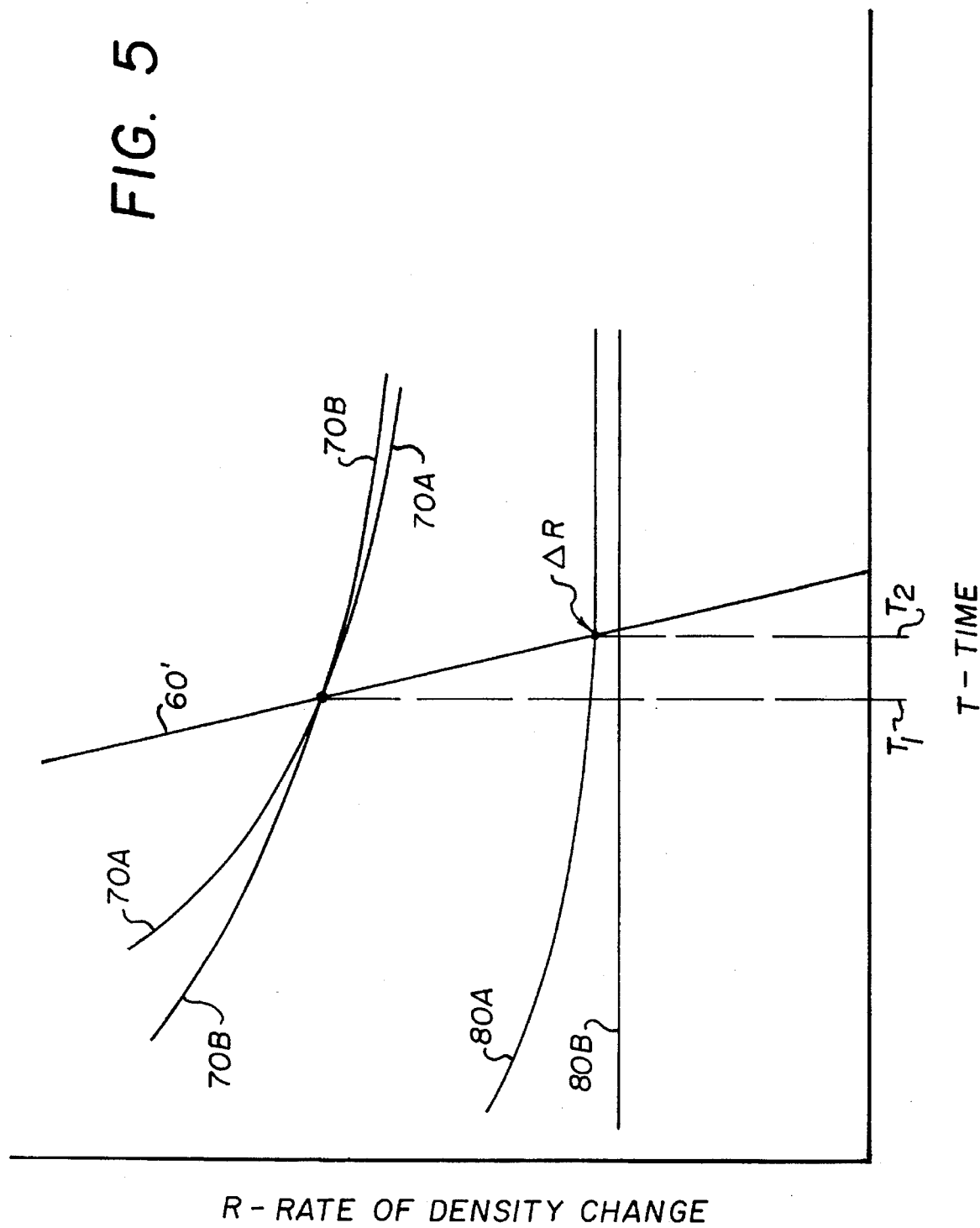
FIG. 5 is a plot similar to that of FIG. 3, but illustrating an alternate embodiment.

If the optimal read time curve 60 is vertical or substantially vertical for a given target immuno-analyte, only one pair of curves needs to be ascertained to identify a single cross-over point for use with all assays of that analyte. This condition is shown in FIG. 5, which also shows a cross-over condition where the paired curves never are equal, but establish a steady state minimum difference $\Delta R$. Thus, in this hypothetical case, a plot of calibration liquids having $C_x$ concentration of analyte and 200 or 5 mg/dl hemoglobin, produces, respectively, curves 70A and 70B that have a cross-over point on time $T_1$, where the rates are substantially equal. When another pair of calibration liquids at five time $C_x$ are plotted, curves 80A and 80B result (curve 80A being for a liquid with non-negligible amounts of 180 mg/dl of hemoglobin). The cross-over point in time is then ascertained to be time $T_2$, where a steady-state minimum difference to ΔR is first obtained. This produces a curve (straight line) 60' of optimal read times that is approximately vertical. Hence, any one of the two read times $T_1$ or $T_2$ is selected to be used thereafter as the optimal read time for all testing of patient sample liquids for this particular immunoassay. (The other time points on curve 60' are then ignored.) Such a process of selecting only one optimal read time is best used, of course, when curve 60' is exactly vertical. However, it is a useful approximation if $T_2-T_1$ varies no more than about 10 seconds over the normal concentration range of the target immuno-analyte.

EXAMPLES

The following examples used the digoxin and phenytoin slide test elements set forth above, tested on an "Ektachem E-250" analyzer available from Clinical Diagnostics Division, formerly of Eastman Kodak Co., using calibration liquids that were spiked with the noted amount of analyte and with zero, or the noted amounts of hemoglobin.

Example 1

Phenytoin

In this example, the calibration liquids had the following formulas:
Liquid 1
To a 1% polyvinylpyrrolidone (PVP) matrix, was added 2.0 µg/L of phenytoin, and this was split into 2 parts one of which had no amount of hemoglobin, and the other which had 250 mg/dl of hemoglobin, to form a pair of liquids.
Liquid 2
To a 1% PVP matrix, 12.0 µg/mL of phenytoin, was added. This was split into two parts, to which was added, in one part, no amount of hemoglobin, and to the other part, 250 mg/dl of hemoglobin, to form a pair of liquids.
Liquid 3
To a 1% PVP matrix, 40 µg/mL of phenytoin was added. This was split into two parts, to which was added, in one part, no amount of hemoglobin, and to the other part, 250 mg/dl of hemoglobin, to form a pair of liquids.

Figure 6:
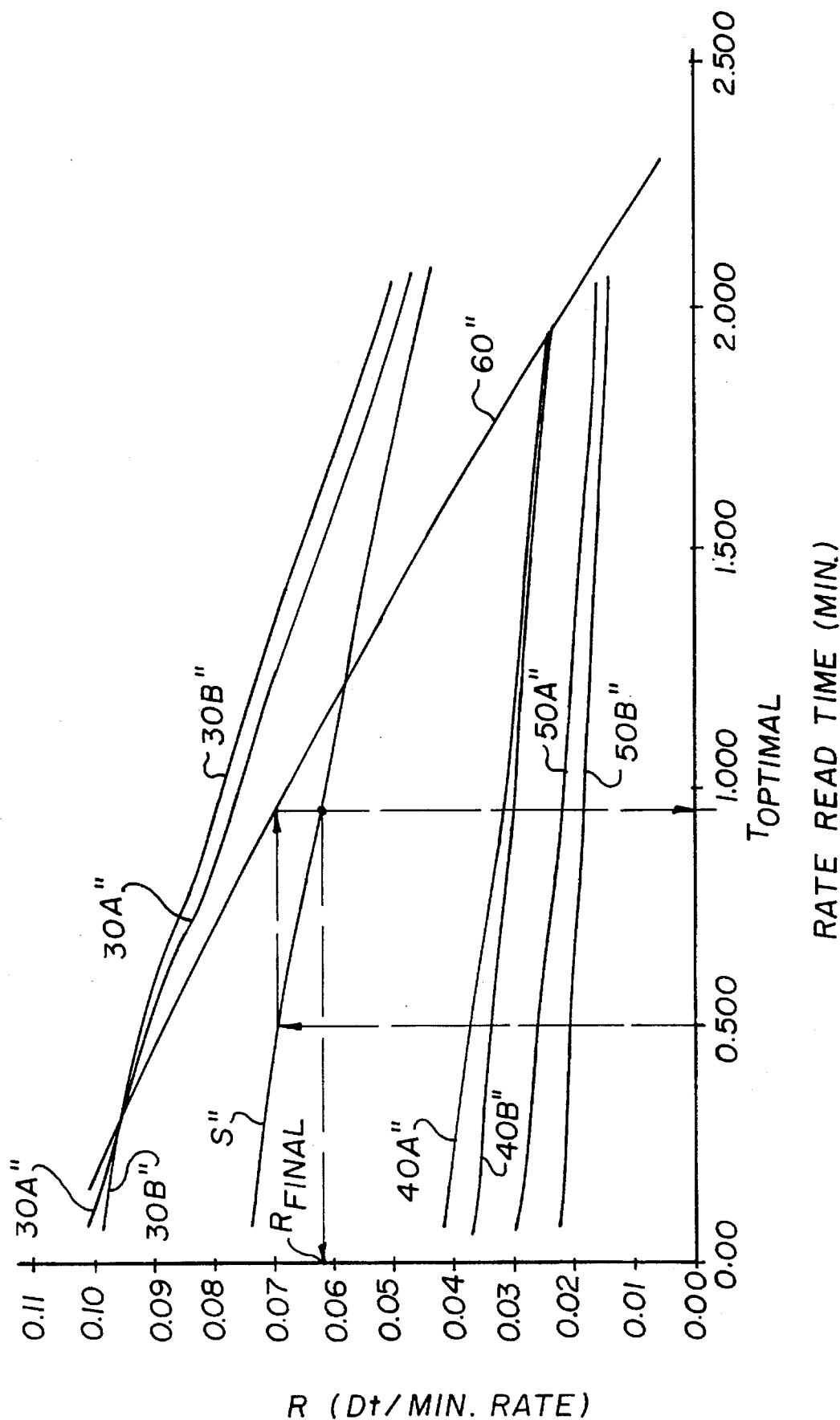

FIG. 6 illustrates the calibration plot and the curve 6041 of the optimal read time achieved by the three pairs of calibration liquids, shown as curves 30A", 30B"; 40A", 40B"; and 50A", 50B". That is, curves 30A" and 30B" are for Liquid 1 the contents of which are described above, and curves 40A", 40B" are for Liquid 2 and curves 50A", 50B" for Liquid 3. In each set, the A curves represent the appropriate Liquid with 250 mg/dL of hemoglobin present, and the B curves represent the appropriate liquid with ZERO amounts of hemoglobin present. (The reaction start time was 0.3 minutes prior to Time=0 sec. in FIGS. 6 and 7.) The amount of phenytoin added to each calibration liquid is noted on the plot. Curve 60" was then used as the optimal read time value, when detecting an initial rate $R_i$, say $R_i=0.07$ at time 0.5 minutes. This then produced a $T_{optimal}$ of about 0.88 minutes, which is then used to read off curve S" for an actual sample, a $R_{final}$ rate reading of 0.063. This $R_{final}$ is converted to a calculated phenytoin concentration of about 7.9 µg/mL.

(Curve 60" can be expressed mathematically as follows:

A $T_{opt}=2.41-20.625$ (rate init.), where $T_{opt}$=the read time derived for any rate of change reading, and $\text{rate}_{init}$ is the reading obtained early on as an initial value, e.g., at 0.5 min.)

The utility of FIG. 6 can also be demonstrated using just the calibrators. Consider first the results if all readings were arbitrarily made, as is conventional, at a fixed time, say 1 minute. In that case, the results are as follows:

TABLE 1

| Drug Level | Rate @ 1.0 min. (Dt/min.) | Hemoglobin Level (mg/dL) | Prediction (µg/mL) | Bias (µg/mL) |
|---|---|---|---|---|
| Liquid 1 | 0.080 | 0 | 5.00 | — |
| Liquid 1 | 0.076 | 250 | 5.45 | 0.45 |
| Liquid 2 | 0.031 | 0 | 20.0 | — |
| Liquid 2 | 0.033 | 250 | 17.6 | −2.4 |
| Liquid 3 | 0.018 | 0 | 40.0 | — |
| Liquid 3 | 0.023 | 250 | 29.1 | −10.9 |

The bias in Table 1 comes from the fact that a time of reading of 1 minute is too late for the liquid 1 case, and too early for liquids 2 and 3, regarding their cross-over times, something that would, of course be unknown if they were samples instead of calibrators.

If, however, equation A above is used, and the very first data points of the curves are used as the "$\text{rate}_{init}$", the results become those shown in Table 2, with much improved biases:

TABLE 2

| Drug Level | Initial Rate | $T_{opt}$ | $\text{Rate}_{opt}$ | Hgb | Prediction (µg/mL) | Bias (µg/mL) |
|---|---|---|---|---|---|---|
| Liquid 1 | 0.098 | 0.39 | 0.094 | 0 | 5.00 | — |
| Liquid 1 | 0.100 | 0.35 | 0.095 | 250 | 4.94 | −0.06 |
| Liquid 2 | 0.036 | 1.67 | 0.027 | 0 | 20.0 | — |
| Liquid 2 | 0.042 | 1.55 | 0.028 | 250 | 19.2 | −0.8 |
| Liquid 3 | 0.022 | 1.96 | 0.015 | 0 | 40.0 | — |
| Liquid 3 | 0.029 | 1.81 | 0.017 | 250 | 34.9 | −5.1 |

Alternatively, the phenytoin assays can be calibrated and assayed in the manner described in the next example, although it clearly is not optimal since the ends of the range are not optimized.

Example 2

Similar calibration curves, FIG. 7, were created in a manner similar to that of Example 1, using digoxin test elements and calibration liquids spiked with digoxin.

Thus, curves 30A''' and 30B''' represent Liquid 1 prepared as described for Example 1, except that the analyte was 1 ng/mL of digoxin. Curves 40A''' and 40B''' represent Liquid 2 prepared as described for Example 1, except that the analyte was 2 ng/mL of digoxin. Curves 50A''' and 50B''' represent Liquid 3, prepared as described for Example 1, except that the analyte was 4 ng/mL of digoxin. As in the case of FIG. 6, the "A" curves are the respective liquids with 250 mg/dL of hemoglobin present, and the "B" curves have zero amounts of hemoglobin present.

An optimal read time curve 60''' was plotted as shown. This curve is sufficiently vertical as to justify the selection of a single optimal point in time for all assays of digoxin. Hence, tests were run successfully using $T_{optimal}$ of 0.7 minutes measured from the start of the reaction, for all concentrations of digoxin.

(The curve 60''' has the following mathematical formula:
$\underline{B}$ $T_{opt}$=0.719–2.75(rate$_{init}$).)

As further illustration, the calibrations of FIG. 7 were also treated as "unknowns", using an arbitrary read time of 0.5 minutes. The results appear in Table 3 as follows:

TABLE 3

| Drug Level | Rate @ 0.5 min. (Dt/min.) | Hemoglobin Level | Prediction (ng/mL) | Bias (ng/mL) |
|---|---|---|---|---|
| Liquid 1 | 0.113 | 0 | 1.00 | — |
| Liquid 1 | 0.110 | 250 | 1.11 | 0.11 |
| Liquid 2 | 0.094 | 0 | 2.00 | — |
| Liquid 2 | 0.092 | 250 | 2.19 | 0.19 |
| Liquid 3 | 0.080 | 0 | 4.00 | — |
| Liquid 3 | 0.080 | 250 | 4.00 | 0.00 |

(The zero bias for Liquid 3 results from the lucky coincidence of 0.5 minutes and the cross-over time for Liquid 3.)

If on the other hand, equation B is used, along with the very first data points of each curve as the "rate$_{init}$", then the results occur as follows, Table 4, with an improved bias compared to that of Table 3:

TABLE 4

| Drug Level | Initial Rate | $T_{opt}$ | Rate$_{opt}$ | Hgb | Prediction (ng/mL) | Bias (ng/mL) |
|---|---|---|---|---|---|---|
| Liquid 1 | 0.123 | 0.38 | 0.119 | 0 | 1.00 | — |
| Liquid 1 | 0.130 | 0.36 | 0.120 | 250 | 0.97 | −0.03 |
| Liquid 2 | 0.100 | 0.44 | 0.096 | 0 | 2.00 | — |
| Liquid 2 | 0.107 | 0.42 | 0.960 | 250 | 2.00 | 0.00 |
| Liquid 3 | 0.083 | 0.49 | 0.080 | 0 | 4.00 | — |
| Liquid 3 | 0.090 | 0.47 | 0.080 | 250 | 4.00 | 0.00 |

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

What is claimed is:

1. A method of reducing bias caused by a known interferent in a peroxidase-labeled immunoassay using a dry analytical element, the method comprising:

a) providing a single generation of dry analytical elements for determining an analyte in a liquid sample, each dry analytical element comprising in one or more layers (i) a predetermined amount of a labeled immunoreactant comprising peroxidase coupled to an immunoreactant selected from the group consisting of the analyte, an analyte analog and a specific binding partner which specifically binds to the analyte and the analyte analog, (ii) an immobilized immunoreactant which specifically binds to a member selected from the group consisting of the analyte, the analyte analog and the specific binding partner, and (iii) a substrate that reacts with the peroxidase to produce a detectable product;

b) providing a first set of calibrators, the first set comprising (i) a first calibrator comprising a known first amount of the analyte without a detectable amount of the known interferent present, and (ii) a second calibrator comprising the same known first amount of the analyte with a detectable first known amount of the known interferent present;

c) individually contacting said first calibrator and said second calibrator of the first set with at least one dry analytical element from the single generation and measuring the rate of change in reflectance density per unit time for each of the first and the second calibrators;

d) calculating a cross-over time point at which the rate of change in reflectance density per unit time for the first calibrator either (i) matches the rate of change in reflectance density per unit time for the second calibrator of the first set or (ii) first reaches a constant minimum difference from the rate of change in reflectance density per unit time for the second calibrator of the first set; and e) contacting the liquid sample to another dry analytical element from the single generation and initiating measurement of the rate of change in reflectance density per unit time caused by the analyte in the liquid sample at the cross-over time point calculated in step d) to reduce any bias caused by any of the known interferent which may be present in the liquid sample.

2. A method as defined in claim 1, wherein said known interferent is hemoglobin.

3. A method as defined in claim 1, wherein said analyte is selected from the group consisting of phenytoin and digoxin.

* * * * *